United States Patent [19]

Barrette et al.

[11] Patent Number: 5,476,466
[45] Date of Patent: Dec. 19, 1995

[54] ORTHOPAEDIC POSITIONING INSTRUMENT

[75] Inventors: John J. Barrette; Philip H. Cripe, both of Warsaw, Ind.; Jeffrey A. Kantor, Albany, N.Y.; John P. Maryan, Anderson, Ind.; J. Gordon Shutek, Austin, Tex.

[73] Assignee: Zimmer, Inc., Warsaw, Ind.

[21] Appl. No.: 94,635

[22] Filed: Jul. 20, 1993

[51] Int. Cl.⁶ .................................................. A61F 5/00
[52] U.S. Cl. ............................................ 686/86; 606/99
[58] Field of Search ............................... 606/86, 87, 88, 606/99, 100, 62–68

[56] References Cited

U.S. PATENT DOCUMENTS

| | | | |
|---|---|---|---|
| 2,528,941 | 11/1950 | Bassett | 606/99 |
| 2,638,092 | 5/1953 | Dorr | 606/99 |
| 3,585,994 | 6/1971 | Huggler | 606/100 |
| 3,801,989 | 4/1974 | McKee | 3/1 |
| 3,834,393 | 9/1974 | Goggins | 606/100 |
| 3,857,389 | 12/1974 | Amstutz | 128/92 EC |
| 4,134,157 | 1/1979 | Laure | 606/86 |
| 4,153,053 | 5/1979 | Figallo | 606/100 |
| 4,222,382 | 9/1980 | Antonsson et al. | 128/303 R |
| 4,406,023 | 9/1983 | Harris | 3/1.912 |
| 4,549,319 | 10/1985 | Meyer | 623/22 |
| 4,551,863 | 11/1985 | Murray | 623/23 |
| 4,592,346 | 6/1986 | Jurgutis | 128/92 B |
| 4,642,121 | 2/1987 | Keller | 623/18 |
| 4,686,971 | 8/1987 | Harris et al. | 128/92 VT |
| 4,792,339 | 12/1988 | Tepi | 623/23 |
| 4,813,962 | 3/1989 | Deckner et al. | 623/23 |
| 4,834,081 | 5/1989 | Van Zile | 128/92 VT |
| 4,904,269 | 2/1990 | Elloy et al. | 623/23 |
| 4,919,153 | 4/1990 | Chin | 606/93 |
| 4,919,679 | 4/1990 | Averill et al. | 623/23 |
| 4,936,863 | 6/1990 | Hofmann | 623/23 |
| 4,993,410 | 2/1991 | Kimsey | 606/100 |
| 5,059,196 | 10/1991 | Coates | 606/99 |
| 5,064,427 | 11/1991 | Burkinshaw | 606/99 |
| 5,116,335 | 5/1992 | Hannon et al. | 606/62 |
| 5,171,324 | 12/1992 | Campana et al. | 623/23 |
| 5,190,549 | 3/1993 | Miller et al. | 606/85 |
| 5,190,550 | 3/1993 | Miller et al. | 606/85 |
| 5,196,018 | 3/1993 | Willert et al. | 606/99 |

FOREIGN PATENT DOCUMENTS

| | | |
|---|---|---|
| 0207873A1 | 1/1987 | European Pat. Off. . |
| 0408109A1 | 1/1991 | European Pat. Off. . |
| 2615097A | 5/1987 | France . |
| 2615097 | 11/1988 | France ........ 606/99 |
| WO91/06262 | 5/1991 | WIPO . |

OTHER PUBLICATIONS

Richard Fracture and Orthopadeic Supplied May 27, 1949.
Brochure–Surgical Technique–Harris Precoat Plus Hip System–Zimmer, Inc.–1983.

Primary Examiner—Michael A. Brown
Attorney, Agent, or Firm—Margaret L. Geringer

[57] ABSTRACT

An orthopaedic positioner instrument 1 for positioning an implant 10 or other surgical device which includes a proximal portion with a transverse hole 17 therein. The instrument includes a locator post 53 or 353 adapted to be received in the transverse hole 17 and a first adjustable pressure applying means adapted to selectively apply pressure against a first outer surface, such as a shoulder 13, of an implant 10 to firmly hold the implant or other device 10 onto instrument 1. The instrument 1 may further include a second adjustable pressure applying means adapted to selectively apply pressure against a second surface of the device, such as the medial side 16 of implant 10.

29 Claims, 4 Drawing Sheets

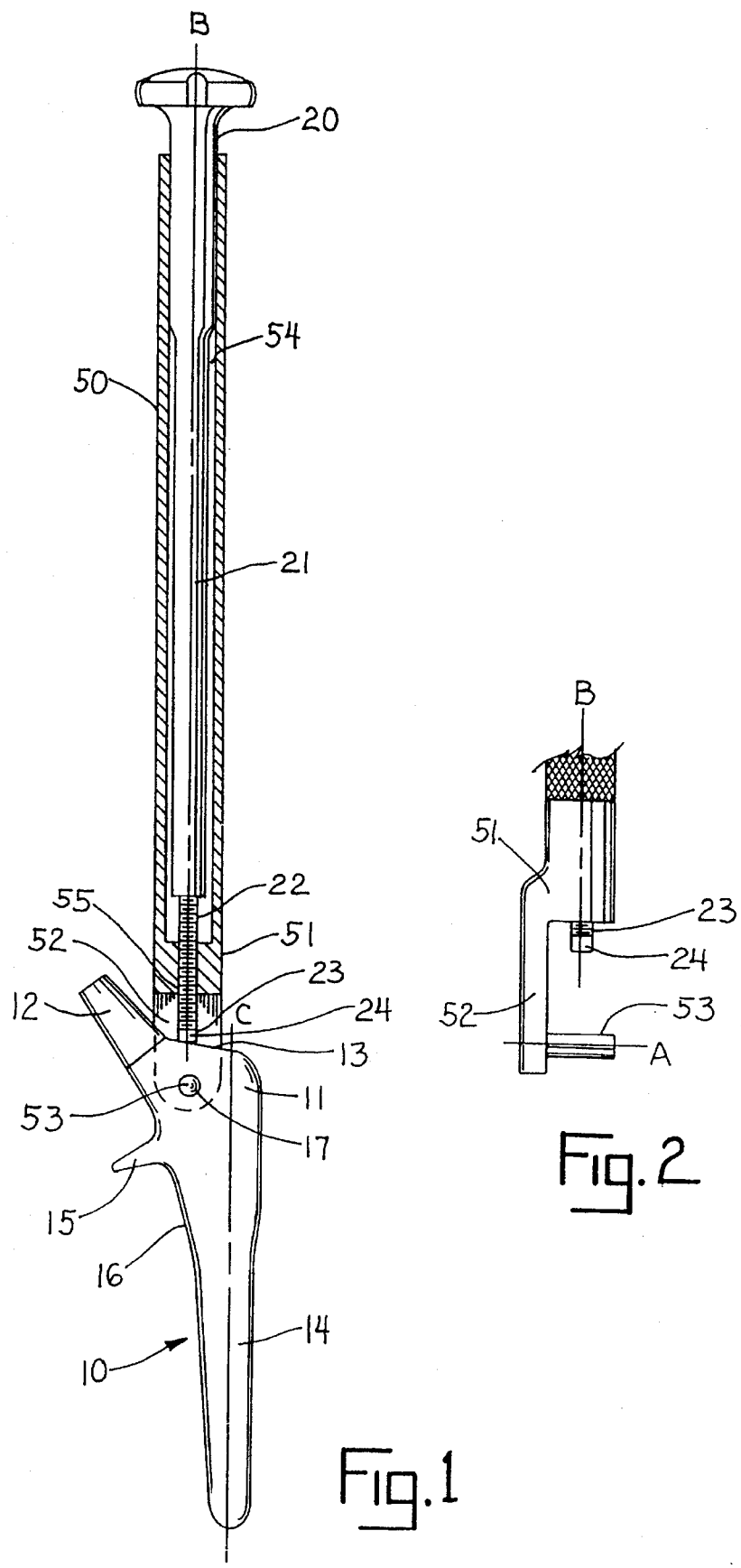

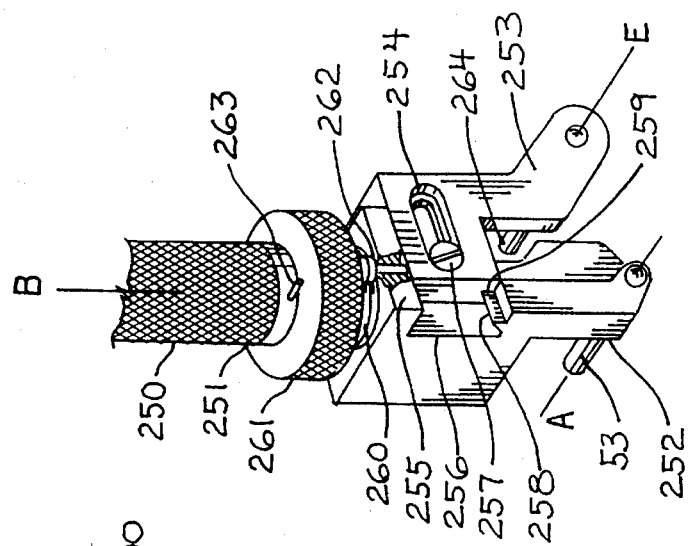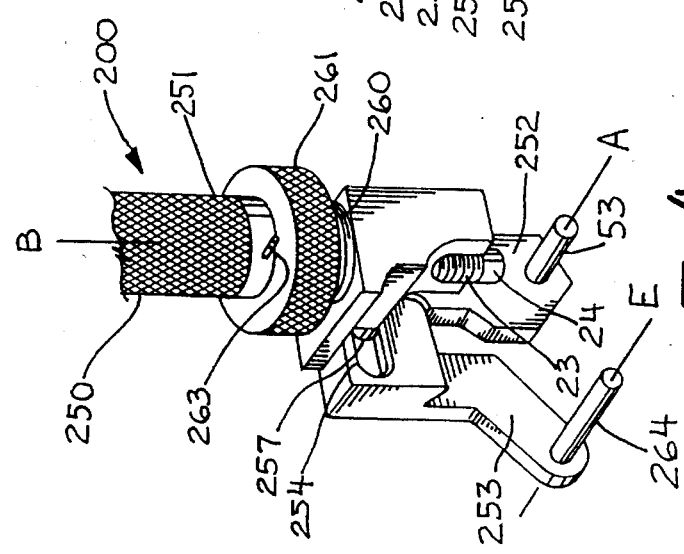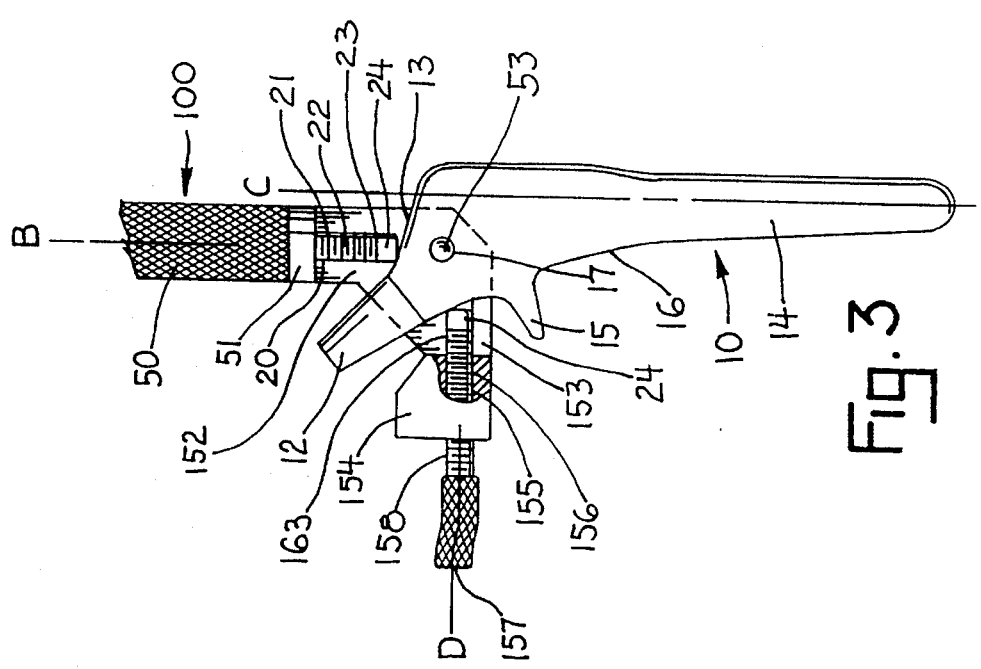

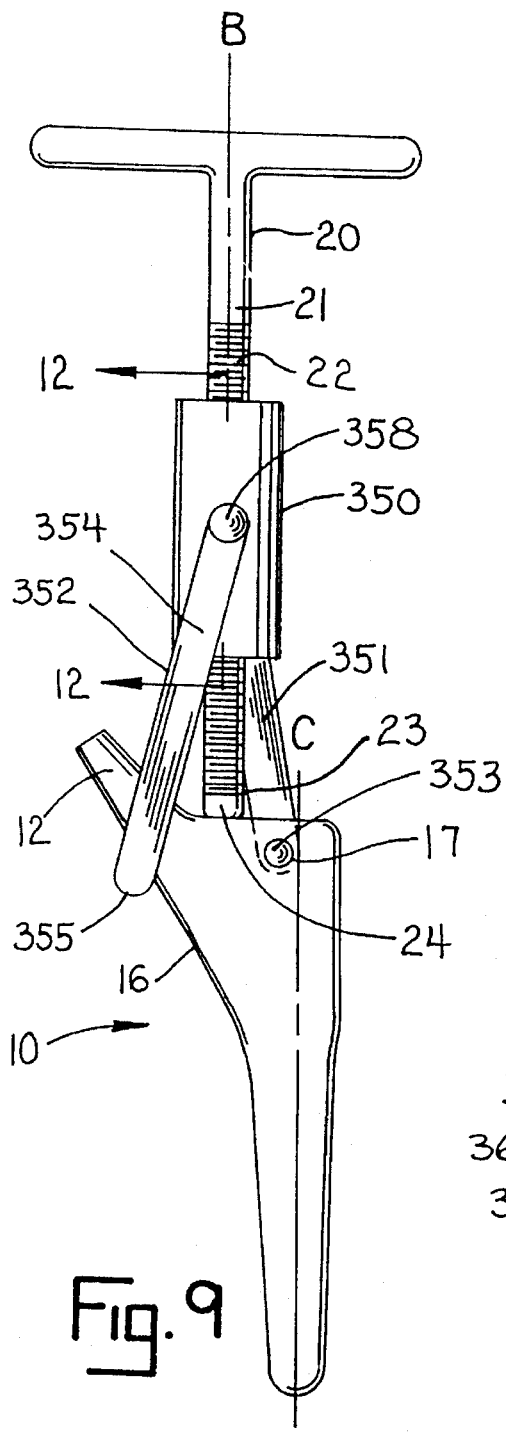
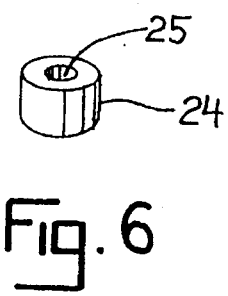
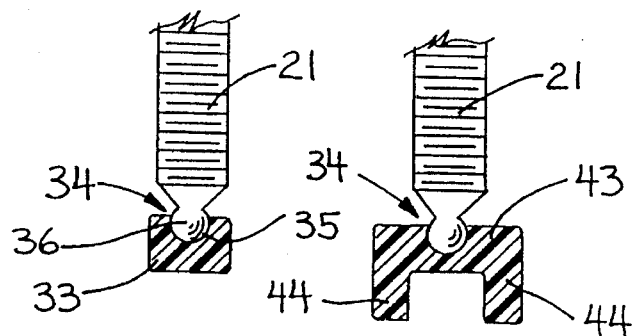

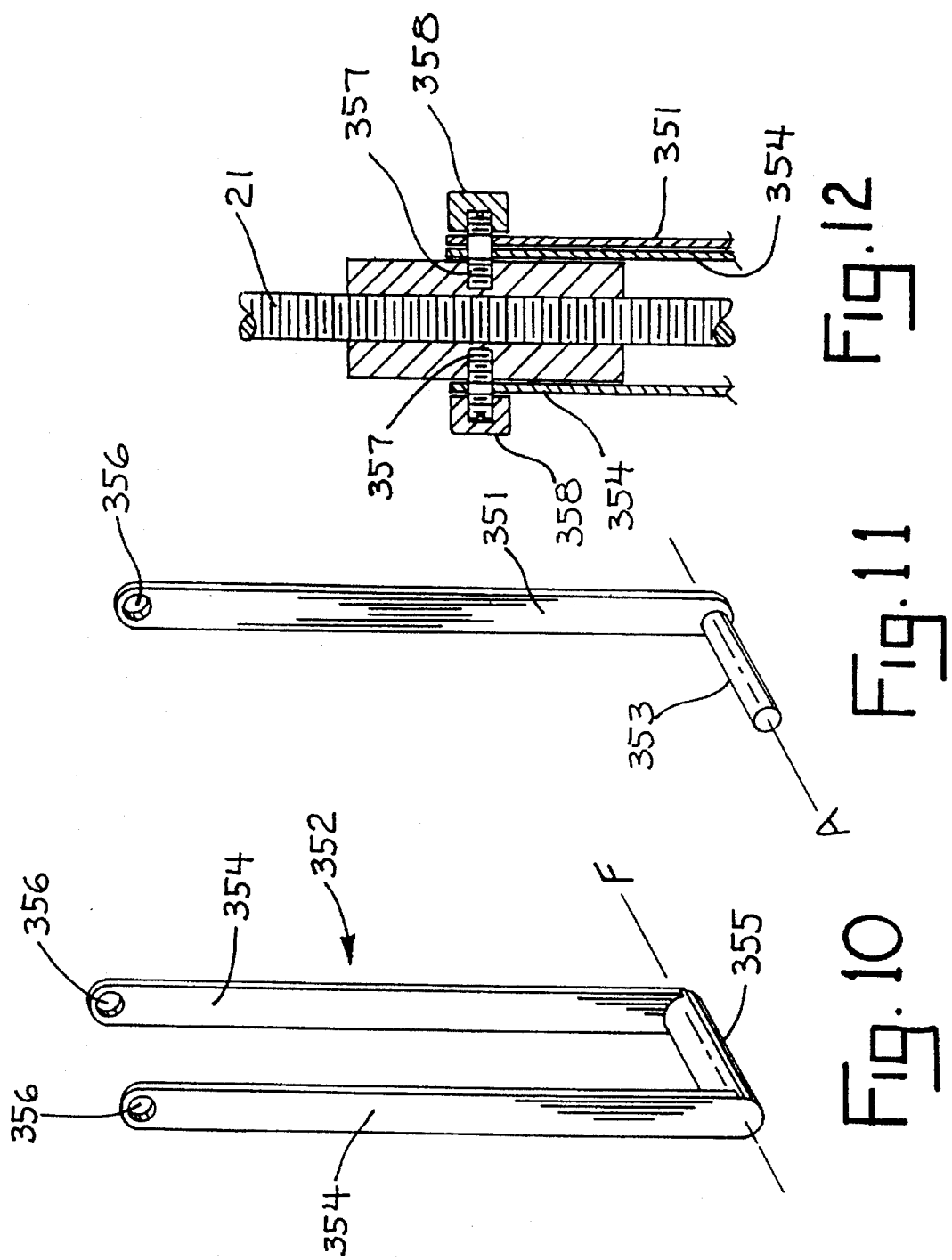

5,476,466

ORTHOPAEDIC POSITIONING INSTRUMENT

FIELD OF INVENTION

The invention relates to the field of orthopaedic positioning instruments. In particular, this invention relates to such instruments for positioning implants or other surgical devices which include a transverse hole in the proximal portion thereof, such as a femoral hip implant which includes a transverse extraction hole therein, or other such devices.

BACKGROUND OF THE INVENTION

In the field of orthopaedics, it is known to utilize various styles of implant positioning instruments to either position or insert an implant or to remove an implant or other such surgical device. For example, many such instruments are secured to the implant or device to be inserted by threading a rod into a hole in the device, such as the following instruments for femoral hip implants: U.S. Pat. Nos. 4,936,863; 4,919,679; 4,549,319; 4,406,023; 3,801,989 and for stemmed implants such as a knee in U.S. Pat. No. 4,834,081.

Other instruments are attached to the neck of a femoral prosthesis, such as in U.S. Pat. Nos. 5,064,427; 4,993,410; 4,904,269; 4,792,339; 4,642,121; 4,551,863; European Patent Applications EP 0 408 109 A1; EP 0 207 873 A1; PCT Application WO 91/06262; French 26 15097A.

In addition, often a transverse extraction hole is provided in an implant to receive hook-shaped instrument in order to remove the implant from the bone, such as in U.S. Pat. No. 4,813,962 or as shown by the Stem Extractor and Slaphammer (Product numbers 6551-02 and 6551-06) sold by Zimmer, Inc.

U.S. Pat. Nos. 5,190,550 and 5,190,549 are also cited to illustrate a locking surgical tool handle for attachment to a surgical tool, such as a femoral rasp. The surgical tool includes a flanged recess for receiving a projection on the inner tension bar of the tool handle. A locking mechanism includes pivotable links attached to the tension bar. The handle includes an unlocked position in which the projection is spaced away from the engagement face of the outer handle body, and a locked position in which the projection on the tension bar pulls an attached tool into tight contact with the outer engagement face of the handle body.

Although not a positioning tool, U.S. Pat. No. 5,171,324 is also cited to illustrate a torque wrench adaptor that locates off of the transverse extraction hole in an implant.

The following additional references are cited to illustrate various other surgical insertion or extraction tools: U.S. Pat. Nos. 5,196,018; 5,116,335; 4,919,153; 4,686,971; 4,592,346; 4,222,382; 3,857,389.

SUMMARY OF THE INVENTION

The present invention provides an orthopaedic positioner instrument for positioning an implant or other surgical device which includes a proximal portion with a transverse hole therein. The instrument includes a locator post adapted to be received in the transverse hole and a first adjustable pressure applying means adapted to selectively apply pressure against a first outer surface, such as a shoulder of an implant to firmly hold the implant or other device in instrument. The instrument may further include a second adjustable pressure applying means adapted to selectively apply pressure against a second surface of the device, such as the medial side of implant.

Accordingly, it is an advantage of the present invention to provide a novel orthopaedic positioning instrument which includes a locator post adapted so be received in a transverse hole of the device to be positioned.

Another advantage of the invention is to provide an adjustable instrument which is suitable for use with a plurality of sizes and styles of devices.

A further advantage of the invention is to provide a simple instrument for positioning an orthopaedic device.

A still further advantage of the invention is to provide an instrument in which the elongated axis of the instrument can be aligned to be substantially parallel to the axis of an elongated stem portion of the device to be positioned.

Another advantage of the invention is to provide a positioning instrument for a femoral implant which allows positioning of the femoral implant with or without the spherical head (not shown) attached.

Still other advantages of the invention will become apparent upon reference to the accompanying drawings.

BRIEF DESCRIPTION OF THE DRAWINGS

FIG. 1 is a front view shown in partial cross-section of a preferred embodiment of an orthopaedic positioning instrument in accordance with the present invention, shown attached to a femoral hip stem implant prosthesis.

FIG. 2 is a partial side view of the instrument of FIG. 1.

FIG. 3 is a partial front view shown in partial cross-section of an alternate embodiment of the instrument shown attached to a femoral implant.

FIG. 4 is a partial front perspective view of a further alternate embodiment of the instrument.

FIG. 5 is a partial rear perspective view of the instrument of FIG. 4.

FIG. 6 is a perspective view of a cap utilized with the instrument of the present invention.

FIG. 7 is an alternate embodiment of the distal tip of the instrument of the present invention.

FIG. 8 is a further alternate embodiment of the distal tip of the instrument of the present invention.

FIG. 9 is a side view of a still further embodiment of the instrument of the present invention shown attached to a femoral implant.

FIG. 10 is a perspective view of the pivotable arm member of the instrument of FIG. 9.

FIG. 11 is a perspective view of the other pivotable arm member of the instrument of FIG. 9.

FIG. 12 is a partial cross-sectional view of the instrument of FIG. 9 taken along lines 12—12.

DESCRIPTION OF THE PREFERRED EMBODIMENT

The preferred embodiments described herein are not intended to be exhaustive or to limit the invention to the precise forms disclosed. Rather it is chosen and described to best explain the invention so that others skilled in the art might utilize its teachings.

Accordingly, FIGS. 1–2 illustrate a preferred embodiment of an orthopaedic positioning instrument 1 in accordance with the present invention. This invention relates to instruments for positioning an orthopaedic implant or other suitable surgical device. The invention will be described wish reference to a prosthetic femoral hip implant; however, it is understood that the invention is not limited thereto, and that the instrument could be adapted for positioning other implants or surgical devices.

The instrument 1 of FIGS. 1 and 2 includes a locator post 53 adapted to be received in a corresponding transverse hole 17 in the proximal portion 11 of femoral implant 10. Instrument 1 further includes a first adjustable pressure applying mechanism adapted to selectively apply pressure against a first outer surface of the implant 10, such as against shoulder 13, to firmly hold the implant 10 onto instrument 1. The first adjustable pressure applying mechanism includes a main handle 20 having an elongated shaft 21 with threads 22 thereon. Shaft 21 has a first distal tip 23 which is adapted to selectively apply pressure to the shoulder 13. Shaft 21 extends through an outer sleeve 50 having a channel 54 therethrough with threads 55. Channel 54 accepts threaded shaft 21 to provide for axial and variable adjustability of shaft 21 within sleeve 50.

The locator post 53 has a first axis A and the shaft 21 of the first adjustable pressure applying means has a second axis B which is transverse (i.e. not parallel) to first axis A of post 53.

A platform 52 extends from a distal end 51 of sleeve 50. Locator post 53 extends from platform 52. Axis A of post 53 is preferably perpendicular to platform 52.

The shaft 21 is threadably retracted away from post 53 to enable transverse hole 17 of implant 10 to be positioned on post 53. Implant 10 includes an elongated stem portion 14 having a third axis C. The third axis C may be visually aligned with second axis B of shaft 21, so that the third axis C and second axis B are substantially parallel. Then shaft 21 is threadably rotated toward post 53 and toward shoulder 13 of implant 10 until it applies enough pressure against the shoulder 13 to firmly hold implant 10 onto instrument 1 to enable implant 10 to be positioned as desired during a surgical procedure.

The instrument 1 may be manufactured by any suitable manufacturing process. Instrument 1 is preferably made of metal, such as stainless steel, although any suitable material may be utilized. A cap 24 as shown in FIG. 6, may be provided with recess 25 to fit over distal end 23 of shaft 21. Recess 25 is preferably of a non-metallic material such as plastic, so that when cap 24 contacts shoulder 13 of implant 10 it does not scratch the surface thereof. Recess 25 of cap 24 may be press-fit onto distal tip 23 otherwise suitably attached.

FIG. 3 illustrates an alternate embodiment 100 of the positioner which includes a second pressure applying mechanism adapted to selectively apply pressure against a second surface, such as on the medial side 16 of implant 10, toward the neck 12 of the implant 10. A collar 15 may or may not be provided extending from medial side 16, as is known in the art.

In the embodiment 100 of FIG. 3 the platform 152 may be extended compared to platform 52 of the embodiment 1 of FIGS. 1–2. Extended platform 152 includes a free end 153 which has a raised block 154 extending therefrom. Raised block 154 includes a channel 155 therethrough which includes threads 156 for accepted threads 158 or rod 157 therein. Threaded rod 157 has a second extending distal tip 163 which also may include a cap 24 thereon to provide the second adjustable pressure applying mechanism. This mechanism is adapted to selectively apply pressure against a second surface, such as medial side 16, of implant 10 to further firmly hole the implant 10 onto instrument 100.

Rod 157 has a fourth elongated axis D which is preferably perpendicular to both axis A of post 53 and axis B of shaft 21.

As with the embodiment 1 of FIGS. 1–2, the shaft 21 and rod 157 can each be threadably rotated toward implant 10 after post 53 has been inserted through transverse hole 17. Once again axis B of shaft 21 may be aligned with axis C of implant 10 so that axes B and C are substantially parallel if desired.

FIGS. 4 and 5 illustrate a further alternate embodiment 200 of the positioner which also includes a second pressure applying mechanism adapted to apply pressure to a second surface, such as medial side 16 of implant 10. Alternate platform 252 is connected to a second adjustable platform extension 253. Extension 253 includes a second post 264 extending therefrom. Second post 264 has a fifth axis E which is substantially parallel to axis A of post 53 and which is substantially perpendicular to axis B of shaft 21. Second post 264 provides a second adjustable pressure applying mechanism adapted to selectively apply pressure against a second surface, such as a medial side 16, of implant 10 to further firmly hold the implant 10 onto instrument 200.

Adjustable platform extension 253 is slidable relative to alternate platform 252, and includes a locking mechanism which is selectively lockable to prevent further sliding of extension 253 when locked and to enable extension 253 to be slidable relative to platform 252 when unlocked. Extension 253 includes a slot 254 therein to accept protruding pin 257 which extends from the back side 255 of platform 252. Protruding pin 257 may be threaded into back 255. Extension 253 rides in recess 256 in back side 255 of platform 252 with groove 259 of extension 253 slidably engaged with corresponding raised rail 258 in recess 256. Protruding pin 257 is adapted to slide in slot 254 when the locking mechanism is unlocked.

The locking mechanism includes a threaded adjustment knob 261 which is attached to threads 260 on distal end 251 of sleeve 250. Knob 261 is threadable into engagement with an abutment pin 262 which applies frictional pressure against adjustable platform extension 253 to lock the extension 253 into a fixed position relative to platform 252. Abutment pin 262 has a smooth shaft and fits in a corresponding hole in back side 255 of platform 252, so that it may extend through and into recess 256 of back side 255 to engage extension 253 when knob 261 is tightened into engagement against pin 262.

Knob 261 is threadably adjustable to unlock and loosen the adjustable platform extension 253 to allow extension 253 to slide relative to platform 252. Sleeve 250 further includes two stop pins 263 to restrict the loosening threaded movement of threaded adjustment knob 261. The limited upward movement of knob 261 also retains the smooth-shafted abutment pin 262 in its corresponding hole in the back side 255 of platform 252.

When utilizing instrument 200, the post 53 is received into locator hale 17. The axis B of shaft 23 may be visually aligned to be substantially parallel with axis C of implant 10. The adjustable platform extension 253 may be slid toward implant 10 until post 264 abuts medial side 16. The knob 261 may then be tightened to apply pressure to medial side 16 of implant 10, and then the shaft 21 is tightened onto shoulder 13 to firmly hold implant 10 in instrument 200.

FIGS. 9–12 illustrate a still further alternate embodiment 300 of the positioner which also includes a second pressure applying mechanism adapted to apply pressure to a second surface, such as medial side 16 of implant 10. Instrument 300 includes a modified outer sleeve 350 with a first pivotable arm 351 extending from sleeve 350. The locator post 353 extends from first arm 351. The second pressure applying means includes a second pivotable arm 352 extending from sleeve 350. Second arm 352 includes two spaced arm members 354 with an interconnecting bar 355 therebetween, with bar 355 forming the second pressure applying means. Bar 355 has a sixth axis F which is substantially parallel to axis A of post 353 and which is substantially perpendicular to axis B of shaft 21. Second arm 352 forms a sling which fits around neck 12, so that bar 355 can contact medial side 16 of implant 10 to apply pressure thereagainst.

First and second arms 351 and 352 are pivotably attached to sleeve 350 via pivot holes 356 which fit over pivot posts 357 extending from sleeve 350. Pivot posts 357 may be threadably attached into sleeve 350 as shown in FIG. 12. Caps 258 may be threadably secured on outer ends of pivot posts 357 to retain first and second arms 351 and 352 on posts 357.

When utilizing instrument 300, the post 353 is received into locator hole 17. The bar 355 is positioned loosely against medial side 16 of implant 10. As the shaft 21 is tightened into engagement with shoulder 13, the spaced apart post 353 and bar 355, which are substantially parallel to each other and which are each pivotably attached to sleeve 350, are drawn toward each other. Thus, the distal tip 23 of shaft 21 applies pressure to shoulder 13 while bar 355 applies inward pressure against medial side 16 of implant 10, while the locator post 353 remains in hole 17. Preferably axis B of shaft 21 is aligned to be substantially parallel with axis C of implant 10, if desirable.

For each of the embodiments 1, 100, 200, and 300 of the invention, the shaft 21 may include an adjustable distal tip 33 as shown in FIG. 7. Tip 33 may be attached to shaft 21 by a toggle mechanism 34 to allow the tip 33 to tilt and adjust to the first surface, such as shoulder 13, of implant 10 since this surface may or may not be slanted relative to the bottom contacting surface of tip 33. The toggle mechanism 34 may include a partial spherical recess 35 which is snap-fit to spherical protrusion 36 on shaft 21, or otherwise pivotably connected.

In addition, for each of the embodiments 1, 100, 200, and 300 of the invention, the shaft 21 may include a saddle-shaped distal tip 43 with a pair of depending legs 44 to straddle the sides of implant 10 which depend from shoulder 13. Saddle tip 43 provides additional support to firmly hold the implant. Saddle tip 43 may also be pivotably attached by a toggle mechanism, such as 34.

These alternate tips 33 and 43 may also be utilized on the second pressure applying mechanism, if appropriate, such as for rod 157 of the embodiment 100 of FIG. 3. These alternate tips 33 and 43 would also be suitably made of a non-metallic material, such as plastic, although any suitable material may be utilized.

It is noted that the locator post 53 or 353 in the various embodiments is cooperatively attached to outer sleeve 50, 250, or 350 accordingly, and is independent of inner elongated shaft 21. Locator post 53 or 353 is preferably a cylindrical post to mate with a cylindrical transverse hole 17. The cylindrical post includes a first end and a second end with the cylindrical portion therebetween, such that the first end of the post 53 or 353 is attached to the instrument and the second oppositely located free end is adapted to be inserted into a circular opening of the transverse hole 17 of the implant 10.

While this invention has been described in terms of a particularly advantageous embodiment, those skilled in the art can appreciate that modifications can be made without departing from the spirit and scope of this invention.

We claim:

1. An instrument for positioning an orthopaedic device in which the device includes a proximal portion with a transverse hole therein the instrument includes a locator post adapted to be received in the transverse hole and a first adjustable pressure applying means having a contact portion adapted to selectively apply pressure against a first outer surface of the device to firmly grip a portion of the orthopaedic device between the contact portion of the first adjustable means and the locator post, and wherein the first adjustable pressure applying means is axially and variably adjustable and wherein the locator post of the instrument has a first axis and the first adjustable pressure applying means has a second axis which is transverse to the first axis of the post.

2. An instrument for positioning an orthopaedic device in which the device includes a proximal portion with a transverse hole therein, wherein the instrument includes a locator post adapted to be received in the transverse hole and a first adjustable pressure applying means adapted to selectively apply pressure against a first outer surface of the device to firmly hold the device onto the instrument, and wherein the first adjustable pressure applying means is axially and variably adjustable and wherein the locator post of the instrument has a first axis and the first adjustable pressure applying means has a second axis which is transverse to the first axis of the post, and wherein the first adjustable pressure applying means includes a main handle having an elongated threaded shaft having a first distal tip which is adapted to selectively apply pressure to the first outer surface, and wherein the shaft extends through an outer sleeve having a threaded channel for accepting the threaded shaft to provide the axial adjustability of the shaft within the sleeve.

3. The instrument of claim 2 wherein a platform extends from a distal end of the sleeve and wherein the locator post extends from the platform.

4. The instrument of claim 3 wherein the post is substantially perpendicular to the platform.

5. The instrument of claim 2 wherein a first pivotable arm extends from the sleeve and wherein the locator post extends from the first arm.

6. The instrument of claim 5 wherein the instrument includes a second adjustable pressure applying means.

7. The instrument of claim 6 wherein the second pressure applying means includes a second pivotable arm means extending from the sleeve and adapted to selectively apply pressure against a second surface of the device to further firmly hold the device onto the instrument.

8. The instrument of claim 7 wherein the second arm means includes two spaced arm members with an interconnecting bar therebetween, wherein the bar forms the second pressure applying means.

9. The instrument of claim 8 wherein the post and bar are spaced apart from each other and are substantially parallel, so that when the shaft of the main handle of the first adjustable pressure applying means is selectively threadably tightened against the first surface of the device, the post and the bar which are each pivotably attached to the sleeve are drawn toward each other to firmly hold the device onto the instrument.

10. The instrument of claim 2 wherein the first distal tip includes a non-metallic tip thereon.

11. The instrument of claim 2 wherein the distal tip is attached to the shaft by a toggle mechanism to enable distal tip to be adjustable relative to the shaft.

12. The instrument of claim 2 wherein the distal tip is saddle-shaped and includes two depending legs to provide additional support to firmly hold the implant.

13. The instrument of claim 2 wherein the locator post is cooperatively attached to the outer sleeve and is independent of the elongated shaft.

14. The instrument of claim 13 wherein the locator post is a cylindrical post with a first end and a second end with a cylindrical portion therebetween, and wherein the first end is attached to the instrument and the second end is a free end oppositely located to the first end, the second free end adapted to be inserted into the transverse hole of the device.

15. An instrument for positioning an orthopaedic device in which the device includes a proximal portion with a transverse hole therein, wherein the instrument includes a locator post adapted to be received in the transverse hole and a first adjustable pressure applying means having a contact portion adapted to selectively apply pressure against a first outer surface of the device to firmly grip a portion, of the orthopaedic device between the contact portion of the first adjustable means and the locator post, and wherein the instrument includes a second adjustable pressure applying means adapted to selectively apply pressure against a second surface of the device.

16. An instrument for positioning an orthopaedic device in which the device includes a proximal portion with a transverse hole therein, wherein the instrument includes a locator post adapted to be received in the transverse hole and a first adjustable pressure applying means adapted to selectively apply pressure against a first outer surface of the device to firmly hold the device onto the instrument, and wherein the first adjustable pressure applying means is axially and variably adjustable and wherein the locator post of the instrument has a first axis and the first adjustable pressure applying means has a second axis which is transverse to the first axis of the post, and wherein the first adjustable pressure applying means includes a main handle having an elongated threaded shaft having a first distal tip which is adapted to selectively apply pressure to the first outer surface and wherein the shaft extends through an outer sleeve having a threaded channel for accepting the threaded shaft to provide the axial adjustability of the shaft within the sleeve, and wherein a platform extends from a distal end of the sleeve and wherein the locator post extends from the platform, and wherein the platform includes a free end which has a raised block extending therefrom, the raised block includes a threaded channel therethrough for accepting a threaded rod therein, the threaded rod has a second extending distal tip which provides a second adjustable pressure applying means adapted to selectively apply pressure against a second surface of the device to further firmly hold the device onto the instrument.

17. An instrument for positioning an orthopaedic device in which the device includes a proximal portion with a transverse hole therein, wherein the instrument includes a locator post adapted to be received in the transverse hole and a first adjustable pressure applying means adapted to selectively apply pressure against a first outer surface of the device to firmly hold the device onto the instrument, and wherein the first adjustable pressure applying means is axially and variably adjustable and wherein the locator post of the instrument has a first axis and the first adjustable pressure applying means has a second axis which is transverse to the first axis of the post, and wherein the first adjustable pressure applying means includes a main handle having an elongated threaded shaft having a first distal tip which is adapted to selectively apply pressure to the first outer surface, and wherein the shaft extends through an outer sleeve having a threaded channel for accepting the threaded shaft to provide the axial adjustability of the shaft within the sleeve, and wherein a platform extends from a distal end of the sleeve and wherein the locator post extends from the platform, and wherein the platform is connected to a second adjustable platform extension which includes a second post extending therefrom, the second post provides a second adjustable pressure applying means adapted to selectively apply pressure against a second surface of the device to further firmly hold the device onto the instrument.

18. The instrument of claim 17 wherein the adjustable platform extension is slidable relative to the platform and includes a locking mechanism which is selectively lockable to prevent further sliding of the adjustable platform extension when locked and to enable the adjustable platform extension to slidable relative to the platform when unlocked.

19. The instrument of claim 18 wherein the adjustable platform extension includes a slot therein to accept a protruding pin which extends from the platform so that the protruding pin can slide in the slot when the locking mechanism is unlocked.

20. The instrument of claim 19 wherein the locking mechanism includes a threaded adjustment knob on the distal end of the sleeve which is threadable into engagement with an abutment pin which applies pressure against the adjustable platform extension to lock the extension into a fixed position relative to the platform.

21. The instrument of claim 20 wherein the adjustment knob is threadably adjustable to unlock and loosen the adjustable platform extension to allow the extension to slide relative to the platform and wherein the sleeve further includes a stop means to restrict the loosening movement of the threaded adjustment knob.

22. An instrument for positioning an orthopaedic device in which the device includes a proximal portion with a transverse hole therein, wherein the instrument includes a locator post adapted to be received in the transverse hole and a first adjustable pressure applying means adapted to selectively apply pressure against a first outer surface of the device to firmly hold the device onto the instrument, and wherein the first adjustable pressure applying means is axially and variably adjustable and wherein the locator post of the instrument has a first axis and the first adjustable pressure applying means has a second axis which is transverse to the first axis of the post, and wherein the device includes an elongated stem portion having a third axis and wherein the third axis of the stem portion is alignable with the second axis of the first axially adjustable pressure applying means of the instrument, so that the third axis and second axis are substantially parallel.

23. An instrument for positioning an orthopaedic device in which the device includes a proximal portion with a transverse hole therein, wherein the instrument includes a locator post adapted to be received in the transverse hole and a first adjustable member having a contact portion adapted to selectively contact first surface of the device to firmly grip a portion of the orthopaedic device between the contact portion of the first adjustable member and the locator post, and wherein the first adjustable member is axially and variably adjustable and wherein the locator post of the instrument has a first axis and the first adjustable member has a second axis which is transverse to the first axis of the post.

24. An instrument for positioning an orthopaedic device in which the device includes a proximal portion with a transverse hole therein, wherein the instrument includes a locator post adapted to be received in the transverse hole and a first adjustable member having a contact portion adapted to selectively contact a first surface of the device to firmly grip a portion of the orthopaedic device between the contact portion of the first adjustable member and the locator post, and wherein the instrument includes a second adjustable member adapted to selectively contact a second surface of the device.

25. An instrument for positioning an orthopaedic device in which the device includes a proximal portion with a transverse hole therein, wherein the instrument includes a locator post adapted to be received in the transverse hole and a first adjustable member adapted to selectively contact a first surface of the device to firmly hold the device onto the instrument, and wherein a platform extends from a distal end of the instrument and wherein the locator post extends from the platform, and wherein the platform includes a free end which has a raised block extending therefrom, the raised block includes a threaded channel therethrough for accepting a threaded rod therein, the threaded rod has a second extending distal tip which provides a second adjustable member adapted to selectively contact a second surface of the device to further firmly hold the device into the instrument.

26. An instrument for positioning an orthopaedic device in which the device includes a proximal portion with a transverse hole therein, wherein the instrument includes a locator post adapted to be received in the transverse hole and a first adjustable member adapted to selectively contact a first surface of the device to firmly hold the device onto the instrument, and wherein a platform extends from a distal end of the instrument and wherein the locator post extends from the platform, and wherein the platform is connected to a second adjustable platform extension which includes a second post extending therefrom, the second post provides a second adjustable member adapted to selectively contact a second surface of the device to further firmly hold the device onto the instrument.

27. A method of firmly holding an orthopaedic device for positioning the device in a surgical procedure including the following steps:
 a) providing the orthopaedic device with a proximal portion having a transverse hole therein;
 b) providing an instrument for positioning the orthopaedic device in which the instrument includes a transverse locator post and a first adjustable member;
 c) first inserting the transverse locator post of the instrument into the transverse hole in the orthopaedic device; and
 d) then adjusting the position of the first adjustable member to enable a contact portion of the first adjustable member to selectively contact a first surface of the orthopaedic device to firmly grip a portion of the orthopaedic device between the contact portion of the first adjustable member and the transverse locator post.

28. The method of claim 27, wherein the method further comprises providing the instrument with a second adjustable member and wherein after the first adjustable member has been adjusted to selectively contact the first surface of the orthopaedic device, then the position of the second adjustable member is adjusted to selectively contact a second surface of the orthopaedic device to further secure and firmly hold the orthopaedic device onto the instrument.

29. An instrument for positioning an orthopaedic device in which the device includes a proximal portion with a transverse hole therein, wherein the instrument includes a locator post adapted to be received in the transverse hole and a first adjustable member adapted to selectively contact a first surface of the device to firmly hold the device onto the instrument, and wherein the first adjustable member is axially and variably adjustable and wherein the locator post of the instrument has a first axis and the first adjustable member has a second axis which is transverse to the first axis of the post.

* * * * *